United States Patent [19]
Antikainen et al.

[11] Patent Number: 5,485,747
[45] Date of Patent: Jan. 23, 1996

[54] METHOD OF MEASUREMENT OF RELATIVE HUMIDITY, IN PARTICULAR IN RADIOSONDES, AND HUMIDITY DETECTORS THAT MAKE USE OF THE METHOD

[75] Inventors: Veijo Antikainen; Ari Paukkunen; Lars Stormbom, all of Vantaa; Hannu Jauhiainen, Espoo; Jorma Ponkala, Ylönkylä, all of Finland

[73] Assignee: Vaisala Oy, Vantaa, Finland

[21] Appl. No.: 294,327

[22] Filed: Aug. 23, 1994

[30] Foreign Application Priority Data

Aug. 23, 1993 [FI] Finland .................................. 933702

[51] Int. Cl.⁶ .................................. G01N 25/56; G01W 1/00
[52] U.S. Cl. .................. 73/335.03; 73/29.01; 73/29.02; 427/79
[58] Field of Search .................. 73/29.01, 335.03, 73/335.04, 29.02, 29.05; 427/79, 80

[56] References Cited

U.S. PATENT DOCUMENTS

| | | | |
|---|---|---|---|
| 3,075,385 | 1/1963 | Stover | 73/29.02 |
| 3,168,829 | 2/1965 | Nelson | 73/335.04 |
| 3,350,941 | 11/1967 | Misevich | 73/335.04 |
| 3,559,456 | 2/1971 | Lomker et al. | 73/29.05 |
| 4,011,538 | 3/1977 | Froemel | 338/35 |
| 4,482,581 | 11/1984 | Lorin et al. | 427/79 |
| 4,603,455 | 8/1986 | Woest et al. | 29/25.42 |
| 4,723,439 | 2/1988 | Asakura et al. | 73/29 |
| 4,931,897 | 6/1990 | Tsukamoto et al. | 361/313 |
| 5,036,704 | 8/1991 | Pusatcioglu et al. | 73/336.5 |
| 5,048,336 | 9/1991 | Sugihara et al. | 73/336.5 |
| 5,296,819 | 3/1994 | Kuroiwa | 324/670 |

FOREIGN PATENT DOCUMENTS

| | | | |
|---|---|---|---|
| 0356682 | 7/1989 | European Pat. Off. | |
| 48229 | 1/1974 | Finland | 73/29 |
| 148229 | 4/1974 | Finland | |
| 158402 | 9/1980 | Finland | |
| 185770 | 2/1992 | Finland | |
| 3911812 | 10/1990 | Germany | |
| 3923595 | 12/1990 | Germany | |
| 0135945 | 8/1983 | Japan | 73/335.03 |
| 597955 | 3/1978 | U.S.S.R. | 73/335.03 |

OTHER PUBLICATIONS

English Abstract for DE 3911812, Derwent WPI.
English Abstract for DE 3923595, Derwent WPI.

*Primary Examiner*—Hezron E. Williams
*Assistant Examiner*—J. David Wiggins
*Attorney, Agent, or Firm*—Jones & Askew

[57] ABSTRACT

Method, in particular in radiosondes, for measurement of relative humidity by using a capacitive humidity detector (10) or a combination of detectors ($10_1$, $10_2$; 10P), as well as humidity detectors. In the detector, between the capacitor plates, an insulating material (12) is used, whose permittivity is a function of the amount of water absorbed by the insulating material (12). The detector (10) or the combination of detectors is heated in order to remove any ice, frost or condensed humidity deposited on the face and/or in the environment of the detector. The detector capacitance ($C_M$) or a part ($C_1 \ldots C_N$) of same is heated, in time and/or in place, periodically by means of electric current (1). The detecting of the detector capacitance ($C_M$) is carried out without measurement of the detector temperature after the detector capacitance or a part ($C_1 \ldots C_N$) of same has cooled down substantially to the temperature of the environment.

8 Claims, 7 Drawing Sheets

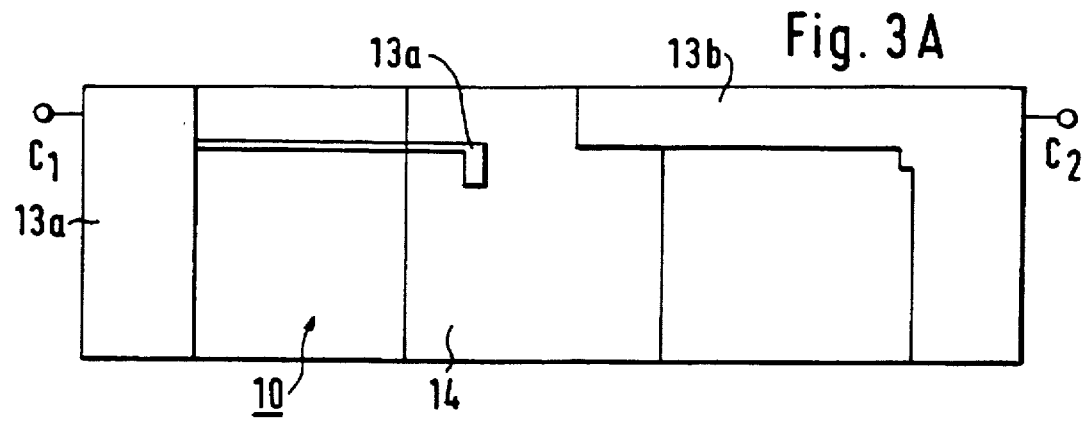
Fig. 3A
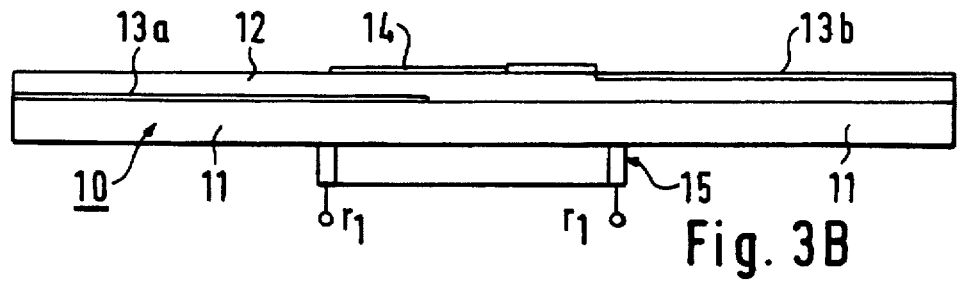
Fig. 3B
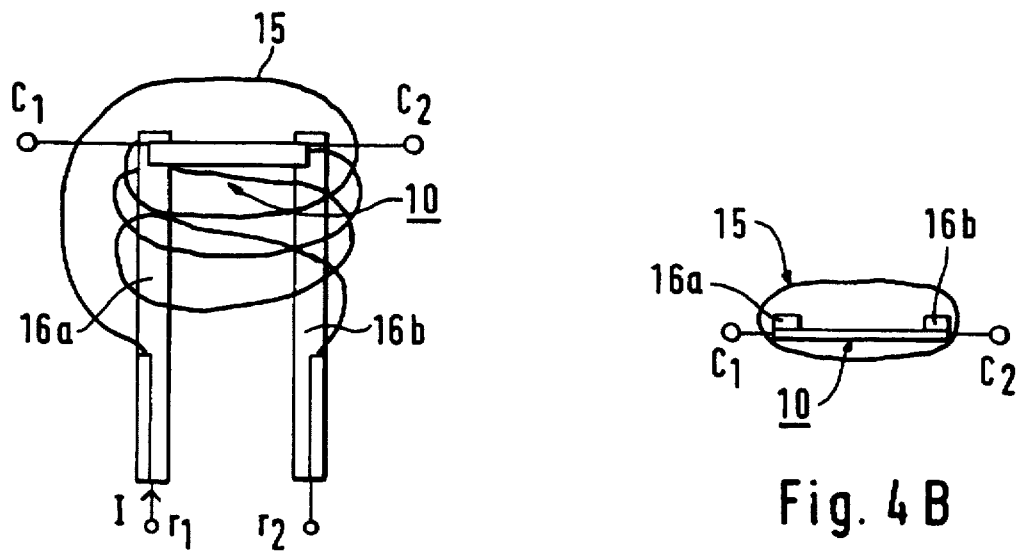
Fig. 4A
Fig. 4B

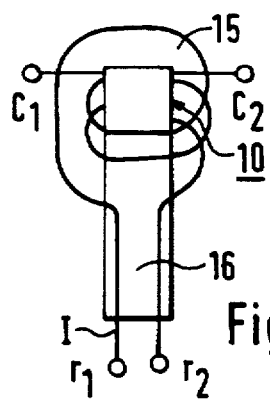
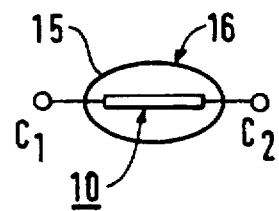
Fig. 5A
Fig. 5B
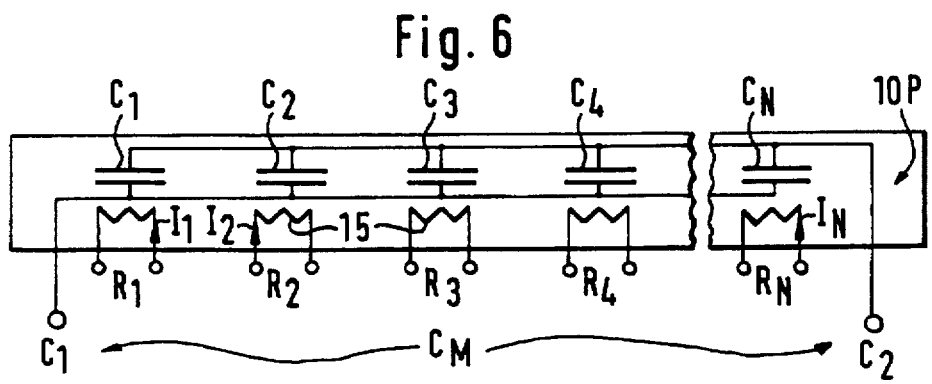
Fig. 6
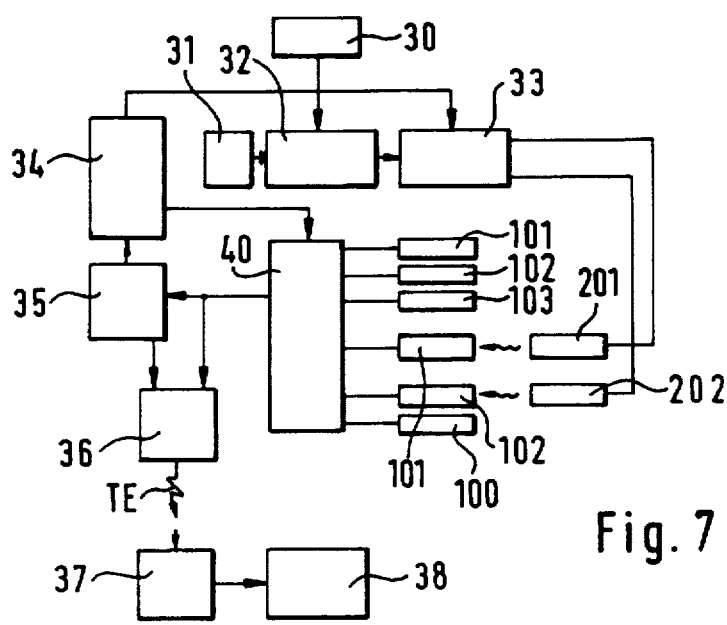
Fig. 7

METHOD OF MEASUREMENT OF RELATIVE HUMIDITY, IN PARTICULAR IN RADIOSONDES, AND HUMIDITY DETECTORS THAT MAKE USE OF THE METHOD

The invention concerns a method for measurement of relative humidity by using a capacitive humidity detector or a combination of detectors, in particular in radiosondes, in which detector, between the capacitor plates, an insulating material is used, whose permittivity is a function of the amount of water absorbed by said insulating material, and in which method said detector or combination of detectors is heated in order to remove any ice, frost or condensed humidity deposited on the face and/or in the environment of the detector.

Further, the invention concerns a capacitive humidity detector, which comprises a substrate made of an insulating material, onto which substrate the electrode and contact patterns necessary for the formation and connecting of the detector capacitance have been applied, and in which detector, between the detector capacitance electrodes, there is an active insulation film, whose permittivity is a function of the amount of water absorbed by said film.

In the prior art, a number of different electrically detected temperature and humidity detectors are known whose impedance changes as a function of the quantity to be measured. Such humidity detectors are known, e.g., from the U.S. Pat. Nos. 3,168,829 and 3,350,941 and from the applicant's Finnish Patent No. 48,229.

As is known in the prior art, for measurement of temperature, capacitive detectors are used, which are usually based on the fact that the permittivity of the insulating material between the capacitor plates is dependent on the temperature, in which case the capacitance detected from the terminals of the detector also depends on the temperature.

The FI Patent No. 48,229 is related to the prior art concerned in the present invention, in which patent a capacitive humidity detector is described in which the dielectric insulating material is a polymer film, whose permittivity is a function of the amount of water absorbed by the polymer film.

In the detectors described above and also in other detectors based on change in impedance, undesirable phenomena occur, which include freezing and wetting of detectors, radiation error, slowness of the detectors, and hysteresis.

In the applicant's FI Patent No. 58,402, a method is described for reduction of undesirable properties produced by reversible changes in an electric humidity detector based on change in impedance, in particular in a capacitive humidity detector, in which the material sensitive to humidity is an organic polymer, which is heated, at least with higher relative humidities, to a temperature higher than the temperature in the environment of the humidity detector. If necessary, the heating power of the detector can be regulated as a function of the humidity to be measured. In said FI patent, the temperature of the humidity detector and/or the outside temperature is/are measured, and this or these auxiliary quantities are utilized in the computing of the humidity measurement values. In said FI patent it is stated that the heating of the detector can be switched off for the time of the measurement, but it is not stated more specifically in what way and for what purpose this switching-off takes place. In any case, in said FI Patent 58,402, measurement of the temperature of the detector is always required, and the measurement result is corrected on the basis of said measurement of temperature because, owing to its raised temperature, the detector "shows" an excessively low value of relative humidity.

Regarding the prior art, reference is made further to the applicant's FI Patent No. 58,403 (corresponding GB Patent No. 2,047,431), wherein a regulating device in a humidity detector is described, which comprises a bridge connection or equivalent, which includes temperature-dependent resistor elements, by whose means the temperature outside the detector and the temperature $T_s$ of the detector itself are detected, the differential voltage in said bridge connection being used as a feedback signal, by whose means the electric power that heats the detector is regulated. As the heating resistor of the detector, such a resistor element of positive temperature coefficient is used, for example a platinum resistor, as operates at the same time as the sensor of the temperature $T_s$ of the detector. As the sensor of the outside temperature $T_a$, such a resistor-thermistor assembly is used, which is placed in an opposite position in relation to the location of the last-mentioned resistor element at the other branch of the bridge connection, that a certain function $T_s=f(T_a)$ characteristic of each detector type comes true by means of the regulator device.

With respect to the prior art related to the present invention, reference is made further to the applicant's FI Patent No. 85,770 (corresponding U.S. Pat. No. 5,156,045), wherein a method is described in connection with impedance detectors for radiosondes, in which method the temperature of the detector or detectors is measured by means of a thermocouple, in which the connection of one branch of its thermoelements is placed in connection with or at the proximity of, the detector to be measured, and in which thermocouple the connection of the other branch is placed in the atmosphere surrounding the detector, and in which method, by means of said thermocouple, the difference between the temperature prevailing in connection with the detector and the temperature of the surrounding atmosphere is observed, an electric signal that represents said difference acting upon the output signal of the measurement coupling of the radiosonde, which signal includes the information on the meteorological quantity or quantities to be measured by means of the detector or detectors.

The general object of the present invention is further development of the prior-art technique of measurement of relative humidity, in particular in radiosonde applications, so that the drawbacks, to be described in more detail later, are avoided.

It is an object of the invention to provide novel methods of measurement and novel detectors, in particular for radiosonde operation, in which the capacitive humidity detector is subjected to such a high humidity that the detector operation deteriorates and water, frost, and/or ice is/are gathered and condensed on the active face of the detector or on the structures in its environment. When such a situation of disturbance is over, it takes a long time before the water or ice has evaporated, during which period of time the detector, of course, gives an erroneous message, indicating an excessively high humidity. Some of the drawbacks mentioned above can be avoided by means of the heating or the capacitive humidity detector described in the above FI Patent 58,402, but it still remains a problem with no satisfactory solution that, in order that a sufficiently accurate measurement of humidity could be provided, the temperature of the humidity detector must also be known highly accurately. In order that an accuracy of ~1 . . . 2% of measurement of relative-humidity could be achieved, it must be possible to measure the temperature of the detector at a precision of ~0.1° C. In the measurement of the temperature, there may be a higher absolute error, but the difference in temperature as compared with the environment must be known at said precision. Thus, the principal object of the invention is to provide a humidity detector by whose means it is possible to avoid the drawbacks produced by condensing and freezing of water on the face of the humidity detector and/or on the structures in its environment, for example, when a radiosonde flies in a supercooled cloud.

The object of the invention is to provide a method of measurement and detectors by whose means relative humidity can be measured at least at the precision of ~1 . . . 2% mentioned above. It is a further object of the invention to provide a method of measurement and detectors that are particularly well suitable for disposable radiosondes, so that, by means of the method and the detectors of the invention, the detector arrangement can be made simple, of low weight and, in large-volume production, also otherwise economical.

In view of achieving the objectives stated above and those that will come out later, the method of the invention is mainly characterized in that the detector capacitance or a part of same is heated, in time and/or in place, periodically by means of electric current, and that the detecting of the detector capacitance is carried out without measurement of the detector temperature after the detector capacitance or a part of same has cooled down substantially to the temperature of the environment.

A first preferred embodiment of the method of the invention is mainly characterized in that, in the method, two or more separate detectors or a coupling of several component detectors in parallel, or equivalent is employed, that when several separate detectors are used, each detector is heated in its turn, and that the relative humidity is detected primarily on the basis of a detector or its component detectors that has/have cooled sufficiently after said heating.

A second preferred embodiment of the method of the invention is mainly characterized in that, in the method, one detector is used, whose heating period is a fraction of the measurement cycle of the detector or combination of detectors, and that the detecting of the detector capacitance is carried out after the heating cycle in the final stage of the measurement cycle after the detector has had time to be stabilized after said heating stage and to cool substantially to the temperature of its environment, at which time it shows a correct humidity reading.

A first embodiment of the detector in accordance with the invention is mainly characterized in that a conductor pattern that forms a heating resistor and related contact patterns have been applied onto the substrate of the detector so as to pass the electric heating current to said heating resistor.

A second embodiment of the detector in accordance with the invention is mainly characterized in that said surface electrode is connected with contact patterns so that the electric current that heats the detector can be passed through said contact patterns into said surface electrode.

A third embodiment of the detector in accordance with the invention is mainly characterized in that the humidity detector is connected with a resistor wire or resistor piece separate from the detector construction proper, which resistor is arranged to operate as a heating resistor of the humidity detector.

A fourth embodiment of the detector in accordance with the invention is mainly characterized in that the detector comprises a number of component capacitances, which are connected in parallel and/or in series so as to form a detector capacitance to be measured, and that each component capacitance is provided with a heating resistor of its own, into which resistors heating currents can be passed separately so as to heat each of the component capacitances separately.

When the method and the detectors in accordance with the invention are applied, the stage of measurement of the detector temperature and the equipment and computing arrangements necessary for said stage can be omitted completely, as a result of which the steps of carrying out of the method and the detector constructions and the related other systems are simplified substantially and, yet, the above accuracy of measurement is achieved, which is, as a rule, adequate in sonde operation.

In the invention, as heating energy, expressly electric current is used, preferably direct current, which is passed, in accordance with the method of the invention, into a resistive heating resistor or into different combinations of heating resistors placed in connection with the detector or combination of detectors.

The heating of the humidity detector, applied in the invention, is needed in order to remove any frost, ice and water, which is detrimental in view of the measurement of humidity, from the detector. The detector assembly consists of a part that measures the humidity and of a heating part. These may be separate constructions, or some construction of the humidity measurement may also be used for heating. If necessary, the heating capacity may also be regulated in various ways.

In the realization of the heating of the humidity detector in accordance with the invention, measurement and regulation electronics may be used as an addition to an ordinary sonde application. When needed, the necessity of heating is detected, and the heating element itself may operate as the detector of the heating requirement so that ice and/or condensed water produce(s) a change in the heating rate of the element, and the slowing down of the specific resistance of the resistor piece in the element is measured by means of the electronics. The electronic system allows the heating to be continued or switches if off, as necessary. The heating cycle can be carried out once during one measurement cycle of the sonde, or otherwise. The heating capacity can be regulated when necessary. If necessary, the magnitude of the capacity can be measured, for example, by means of a resistor that is heated simultaneously with the heating. This information can also be used as a measure of freezing efficiency or of supersaturation.

A preferred embodiment of the humidity detector in accordance with the invention is characterized by its small size and construction so that a short-time heating pulse spreads to the surface electrode and to its vicinity only. In such a case, the thermal time constant and the humidity time constant of the detector are very short and permit the use of the detector for measurement of humidity directly without correction of errors arising from heating in sonde operation, in which the measurement of humidity takes place, as is known from the prior art, once in about 1.5 seconds. The heating removes any ice and water that interferes with the measurement from the face and/or the vicinity of the humidity detector. The small size of the detector makes the use of radiation protection unnecessary. The cost of manufacture of the detector can also be made lower than with the prior-art detectors.

In the invention, it is possible to use two physically separate detectors or an integrated pair of detectors that are thermally insulated from one another, so that one detector is heated while the relative humidity is being measured by means of the other one, and the other way round, alternatingly. By means of heating, the ice and water detrimental to the measurement of humidity are removed from the detector.

By means of the principle of alternation, the use of a detector that has been heated but has not yet become sufficiently cool for measurements of humidity is avoided, and awkward measurements of the detector temperature and difficulties in compensation computing are eliminated. Also, a possibility is provided for many sorts of timing of heating and regulation of heating capacity. The detector does not have to be so extremely rapid as when pulse heating of one detector is applied, even if the use of this is also possible. A detector that is best suitable for this use is a detector heated by means of a bottom electrode, in which an advantage is the making of the heating resistor in an integrated way in connection with the manufacture of the humidity detector. In such a case, the thermal time constant and the humidity time constant can be made sufficiently short, the transfer of heat becomes good, and the application of the heating capacity to the correct area becomes correct. Small size and integration bring economies of cost in the manufacture. In the electronic system, modifications are required in comparison with the prior art sonde electronics, because the detectors are connected alternatingly to heating or to humidity measurement. If necessary, the heating may also be regulated in different ways. An electronic system that measures both of the humidity detectors constantly is also possible. In such a case, the heating alone is alternated, and the correct humidity is distinguished by means of data processing based on the fact that a warm detector shows a lower reading. It is also possible to use one detector so that it is heated in between, and the incorrect data are rejected and the interpolated "correct" data are substituted for the rejected data.

The invention can also be carded into effect so that several component detectors that measure humidity are connected in parallel. The measurement of relative humidity takes place under parallel connection across all of the capacitive humidity detectors preferably constantly. Each component detector is heated separately one at a time. The error produced by the heating is always reduced to one part per N of the error of one component detector when N component detectors are connected in parallel. The error is reduced further when the detector assembly is calibrated while said heating is in operation normally. The electronic system is needed for the heating and for carrying out the measurement. Such connecting in parallel of detectors can be accomplished with detectors based on the heating of a surface electrode or of a bottom electrode. Also, the applicant's prior-art "Humicap"™ construction is possible if supplemented with a heating resistor, which is either vapour-deposited on the substrate or a resistor piece. The humidity detectors can be integrated on one or several substrates.

In the invention, the advantage is also obtained that various electrical phenomena related to the electric current used for the heating do not interfere with the measurement of the detector capacitance, which is also important in the respect that said detector capacitances used in measurements of relative humidity are quite low, their capacitance value being, as a rule, in the range of 1 . . . 100 pf.

In the following, the invention will be described in detail with reference to some preferred exemplifying embodiments of the invention illustrated in the figures in the accompanying drawing, the invention being by no means strictly confined to the details of said embodiments.

FIG. 3A is a top view of a third embodiment of a detector of the invention.

FIG. 3B shows the same as FIG. 3A as a side view.

FIG. 4A is a side view of a humidity detector in accordance with the invention in which the heating resistor is wound around the detector.

FIG. 4B shows the same as FIG. 4A as a top view.

FIG. 5A is an illustration similar to FIG. 4A of a modification of the detector shown in FIG. 4A.

FIG. 5B is a top view of a detector as shown in FIG. 5A.

FIG. 6 is a schematic illustration of a detector assembly in accordance with the invention in which the detector capacitance is composed of a joint connection of the capacitances in which there are N capacitances connected in parallel.

FIG. 7 is a block diagram illustration of a radiosonde measurement system that makes use of the method of the invention.

Figure 1A:
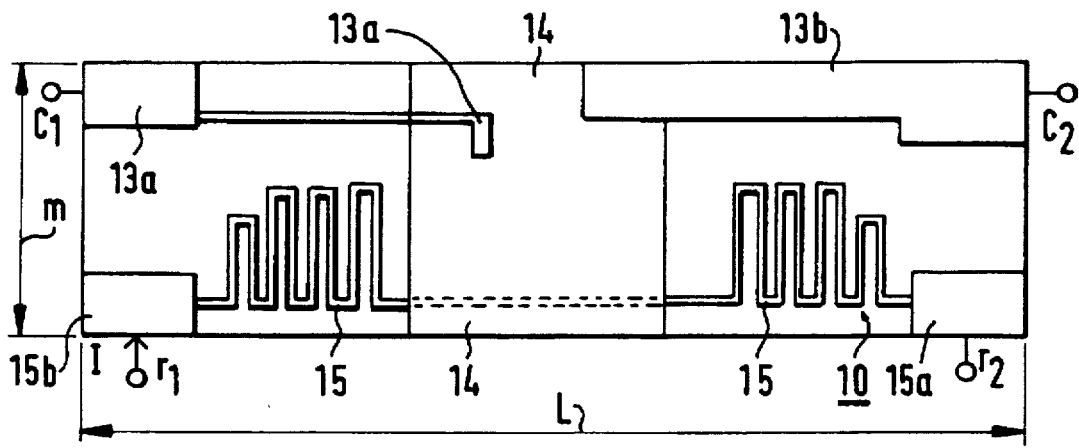
FIG. 1A is a top view of a first embodiment of a detector of the invention.
Figure 1B:
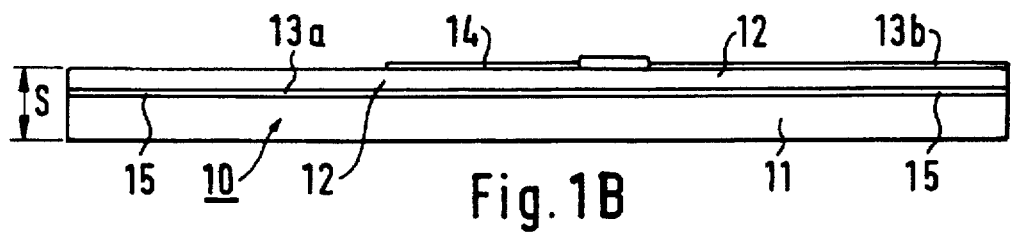
FIG. 1B shows the same as FIG. 1A as a side view.

The humidity detector shown in FIGS. 1A and 1B is constructed on a stable glass substrate 10, onto one of whose plane faces the electrode 13a of the detector capacitance is applied, onto which electrode a plastic film 12 is fitted whose permittivity is a function of the amount of water absorbed by the film 12. Onto the film 12, a surface electrode film 14 is applied, which is penetrable by water but, yet, electrically conductive and which is in galvanic connection with a surface contact 13b. The capacitance. $C_M$ to be measured is detected between the terminals $c_1$ and $c_2$ connected to the contacts 13a and 13b. The detector 10 as shown in FIGS. 1A and 1B is provided with an electrical heating resistor 15, whose conductor pattern is applied onto the same face of the substrate 11 as the bottom electrode 13a. To the heating resistor 15, the electric heating current I, preferably direct current, can be passed through the terminals $r_1$ and $r_2$ connected to the contact patterns 15a and 15b.

Figure 1C:
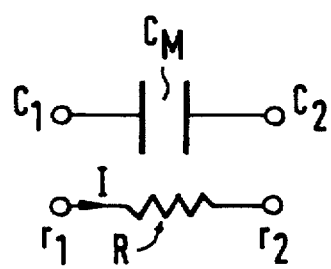
FIG. 1C shows an equivalent circuit of the detector as shown in FIGS. 1A and 1B.

The electric equivalent circuit of the humidity detector 10 as shown in FIGS. 1A and 1B is illustrated in FIG. 1C. The heating current I passed to the heating resistor R produces a heating power $W=I^2 \times R$, which heats the active film 12 of the capacitance to be measured, melts any ice or frost that may be present on it and evaporates any extra moisture from the face of the film 12.

Figure 2A:
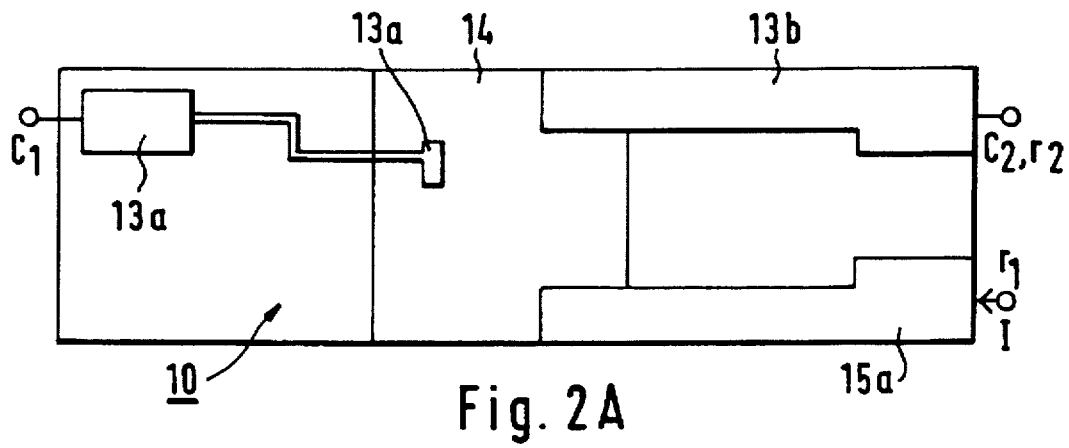
FIG. 2A shows a second embodiment of a detector of the invention.
Figure 2B:
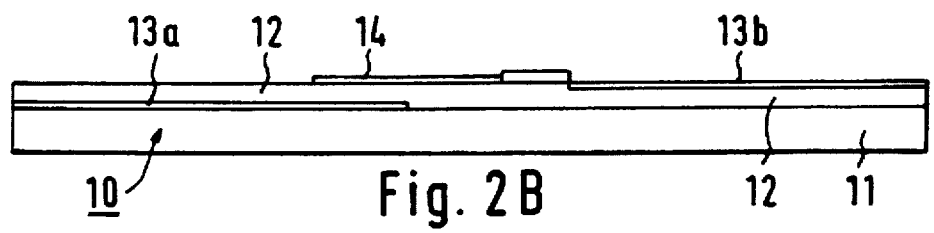
FIG. 2B shows the same as FIG. 2A as a side view.

FIGS. 2A and 2B show a second humidity detector 10 in accordance with the invention, in which no separate heating resistor is used, but the heating resistor R consists of an electrically conductive surface electrode 14. The opposite edges of the surface electrode 14 are connected to conductor patterns 13b and 15a, the heating current I being fed through the terminals $r_1$ and $r_2$ connected to said conductor patterns, which current I, when it flows through the conductive resistive material of the surface electrode 14, produces the desired heating effect $W=I^2 \times R$, wherein R=the resistance measured from the terminals 13a, 15b of the surface electrode.

The surface electrode 14 is a very thin, "perforated" film penetrable by moisture and made, e.g., of gold, which film is, however, electrically continuous and, thus, also electrically conductive.

Figure 2C:
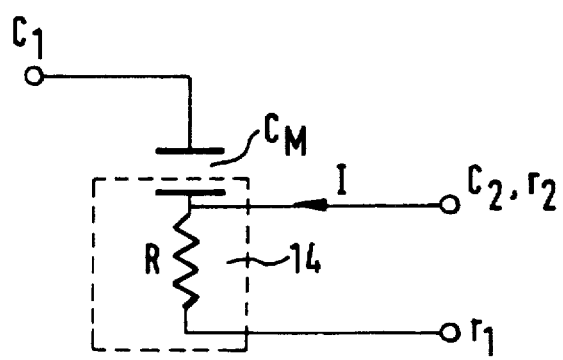
FIG. 2C shows an equivalent circuit of the detector as shown in FIGS. 2A and 2B.

The electric equivalent circuit of the humidity detector 10 as shown in FIGS. 2A and 2B is shown in FIG. 2C, from which it is seen that the capacitance $C_M$ to be measured and the heating resistor R that consists of the surface electrode have a common terminal $c_2=r_2$.

FIGS. 3A and 3B show a detector 10 that is in the other respects similar to FIGS. 1A and 1B except that the heating resistor 15 is placed on the opposite face of the glass substrate 11 in relation to the electrodes 13a, 14 and to the active film 12. The equivalent circuit of the humidity detector as shown in FIGS. 3A and 3B is similar to that shown in FIG. 1C. In view of achieving the objectives of the invention, the measures 1×m×s of the detectors shown in FIGS. 1, 2 and 3 are relatively little, so that both the size and the thermal mass of the detector can be made little and, thus, such that it is heated and cooled sufficiently rapidly. Typically, the dimensions 1×m×s given above are ≈4 mm×1.5 mm×0.2 min.

In FIGS. 4A and 4B, a detector 10 in accordance with the invention is shown that is attached to support strips 16a and 16b, which are made of an insulating material. Around the support strips 16a, 16b and, at the same time, around the active detector 10, a resistor wire 15 is wound, which forms the resistor R that heats the detector, the heating current I being passed to the terminals $r_1$ and $r_2$ of said resistor R. FIGS. 5A and 5B show a heated detector construction which is in the other respects similar to that shown in FIGS. 4A and 4B except that the active detector 10 is attached to a unified strip 16, around which, like around the detector 10, a resistor wire 15 is wound, which forms the heating resistor R of the detector 10. The electric equivalent circuit of the detectors as shown in FIGS. 4 and 5 is similar to that shown in FIG. 1C. Thus, according to FIGS. 4 and 5, the detector 10 proper, the heating resistor 15, and its possible support constructions 16a, 16b are, differing from FIGS. 1 to 3, constructions separate from one another and manufactured in different stages of manufacture. It is an advantage of the constructions as shown in FIGS. 4 and 5 that, as the humidity detector 10, it is possible to use detectors similar to the prior art, for example the detectors marketed by the applicant under the trade mark "Humicup". However, a particular advantage of the constructions as shown in FIGS. 1 to 3 is their small size and low thermal mass, which are of substantial advantage in a number of different applications of the invention, as will come out in more detail later.

FIG. 6 shows a detector assembly 10P in accordance with the invention in which there are N component detector capacitances $C_1 \ldots C_N$, which are connected in parallel with one another. Each component capacitance $C_1 \ldots C_N$ is provided with a heating resistor $R_1 \ldots R_N$ of its own, to each of which resistors a heating current $I_1 \ldots I_N$ can be passed alternatingly and separately (as a rule, $I_1=I_2 \ldots =I_N$). The capacitance to be measured is $C_M=C_1+C_2 \ldots +C_N$. The capacitance $C_M$ to be measured can be detected constantly. The heating of the different component capacitances $C_1 \ldots C_N$ is carried out alternatingly so that one component capacitance $C_1 \ldots C_N$ is always heated while the other capacitances are cooling at the same time. Thus, the error produced by the heating is lowered to one part per N, and yet, from the active face of each component capacitance, the frost and ice can be melted and any extra moisture can be evaporated alternatingly. The error produced by the heating can be reduced further by calibrating the detector while said alternating heating is in its normal operation. When the detector capacitance $C_M$ is measured constantly or substantially constantly, the component capacitances $C_1 \ldots C_N$ are heated, being alternated in a certain repeated cycle $T_0$, for the time $t_o$, and said times are chosen so that $t_o \approx T_0/N$, wherein N is the number of the component capacitances $C_1 \ldots C_N$. If constant measurement is not needed, between the measurement cycles $T_0$ it is possible to use rest cycles and/or cycles in which all the component capacitances $C_1 \ldots C_N$ are heated simultaneously.

FIG. 7 is an illustration of principle in the form of a block diagram of a system of measurement of a radiosonde that makes use of the method of measurement of the invention and of two humidity detectors $10_1$ and $10_2$ in accordance with the invention. The system in accordance with FIG. 7 comprises a sensor element 30, a source of electricity 31, a regulator 32 of the level of heating of the detectors $10_1$, $10_2$, and a distributor 33 of heating current. The system comprises a control unit 34 for measurement and heating, a data processing unit 35 (optional) for the sonde, a telemeter transmitter 36, and measurement electronics 40 for the detectors. Further, the system includes detectors 101, 102 and 103 ... $100_n$ for the physical quantities measured by the radiosonde, such as pressure and temperature and equivalent, and humidity detectors $10_1$ and $10_2$ in accordance with the invention. Said units are placed in the radiosonde rising on support of a gas balloon, and in radio contact through a wireless telemeter link TE with the radio receivers 37 and the data processing units 38 at the ground station. By means of the unit 38, the physical quantities of the atmosphere detected by means of the detectors 101 ... $100_n$, $10_1$ and $10_2$ are processed, indicated and displayed. The unit 33 controls the heater units $20_1$, $20_2$, which heat the humidity detectors $10_1$ and $10_2$ preferably alternatingly so that, in each heating stage, the ice or frost can be melted and the moisture be evaporated from the face of the detector $10_1$ and $10_2$ concerned, and so that the detector capacitance $C_M$ that is being measured has had time to cool to a level sufficiently close to the temperature of the environment, without necessity to measure the temperature of the detector capacitance $C_M$ and, based on said measurement, to carry out a compensation computing of the measurement results. The system shown in FIG. 7 can also be used in connection with a detector as shown in FIG. 6, however, as modified in such a way that the heating is alternated in respect of each of the N pcs. of component detectors $C_1 \ldots C_N$, and the measurement of the capacitance $C_M$ is carried out from the terminals $c_1$ and $c_2$ of the detector illustrated in FIG. 6.

In the system of FIG. 7, the humidity detectors $10_1$ and $10_2$ operate alternatingly as measurement detectors. The system may also operate so that the electronic system 40 measures both of the capacitances $C_M$ of the humidity detectors $10_1$ and $10_2$ constantly, and just the heating of the detectors by means of the units $20_1$ and $20_2$ is alternated. In such a case, the correct humidity observation (cooled detector $10_1$ or $10_2$) is distinguished by means of data processing, based on the fact that an excessively warm detector $10_1$ or $10_2$ shows a lower reading, which is rejected.

Figure 8:
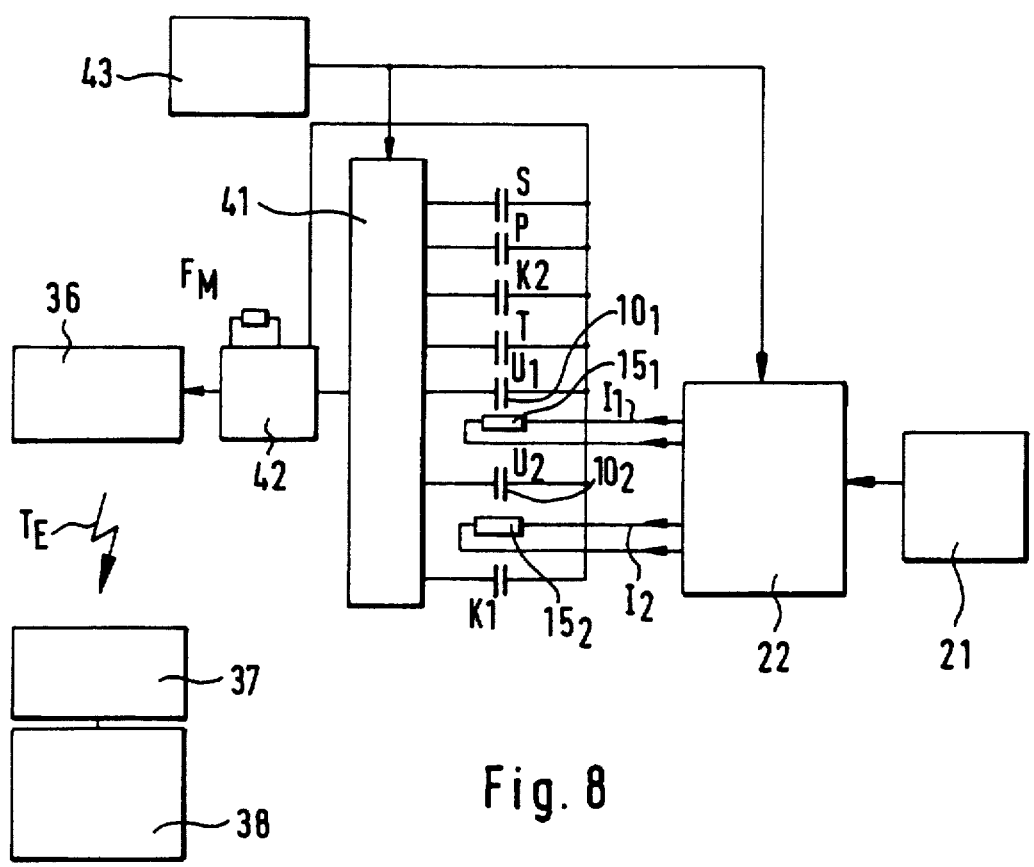
FIG. 8 is a block diagram illustration of a measurement system in accordance with a first preferred embodiment of the invention in which two detector capacitances are used that are heated alternatingly.

FIG. 8 shows a more detailed exemplifying embodiment of the system as shown in FIG. 7. According to FIG. 8, the system comprises a measurement-sequence unit 43, which controls a multiplexer 41 and a control unit 22 for the heating of the detectors $10_1$ and $10_2$, to which control unit the heating power is fed from the unit 21. In connection with the humidity detectors $10_1$ and $10_2$, there are heating resistors $15_1$ and $15_2$, into each of which the heating current $I_1$ and $I_2$ is fed alternatingly (as a rule, $I_1=I_2$), being controlled by the unit 21. The multiplexer 41 connects all the different detectors of the sonde to the measurement and to the telemeter connection TE alternatingly, said detectors being denoted in FIG. 8 with s, p, $k_2$, T, $u_1=10_1$, $u_2=10_2$, and $k_1$. The detector s represents, e.g., the temperature detector of a pressure detector, the detector p a pressure detector, the detector T a temperature detector, and the detectors $k_1$ and $k_2$ represent precisely known reference and calibration detectors. Through the multiplexer 41, said detectors, which are usually capacitive detectors, are connected to a capacitance part which determines the frequency of the RC oscillator 42, whereby the frequency $f_M$ is obtained from the oscillator 42, which frequency is proportional to the quantity to be measured. The radio transmitter 36 is modulated with the frequency $f_M$.

Figure 9:
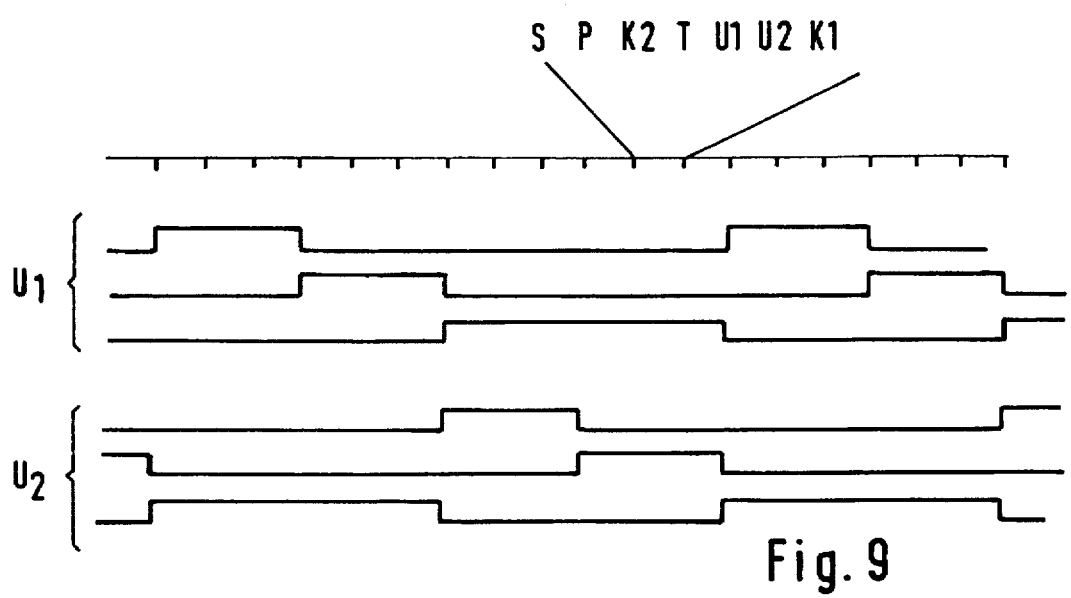
FIG. 9 illustrates the measurement cycles and sequences in the system of measurement as shown in FIG. 8.

The top part of FIG. 9 illustrates the measurement cycles that are repeated one after the other, each of which cycles includes successive readings of the detectors s, p, $k_2$, T, $u_1$, $u_2$, and $k_1$. The bottom part of FIG. 9 shows a pulse diagram illustrating the heating, stabilization and measurement sequences of the detectors $u_1=10_1$ and $u_2=10_2$, so that, when the pulse is up, the operation indicated at the left side in FIG. 9 is being carried out.

In a so-called infrequent-pulse application of the invention, it is possible to use just one detector. In this application, incorrect data are detected as programmed, and interpolation is carried out.

Figure 10:
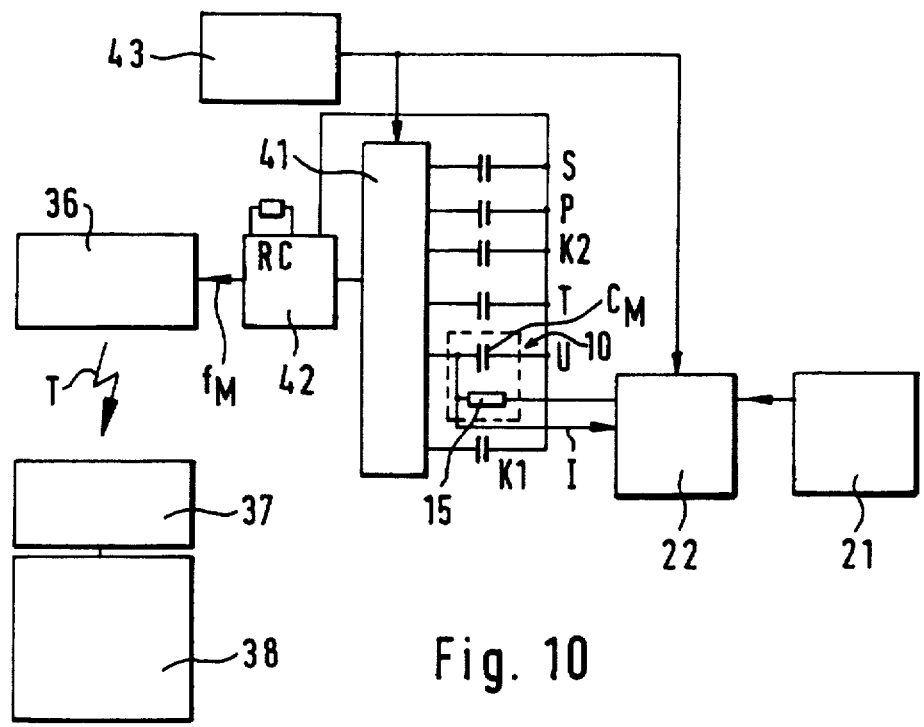
FIG. 10 is a block diagram illustration of a measurement system in accordance with a second preferred embodiment of the invention in which a humidity detector in accordance with a second embodiment is used.

FIG. 10 shows an embodiment of the invention which is in the other respects similar to that shown in FIGS. 8 and 9, except that therein just one humidity detector u=10 is used, which is connected with a heating resistor 15, which is heated from the heating-power unit 21 by means of the heating current I, controlled by the unit 22. The operation of the system of FIG. 10 is in all the other respects similar to that described above in relation to FIGS. 8 and 9.

Figure 11:
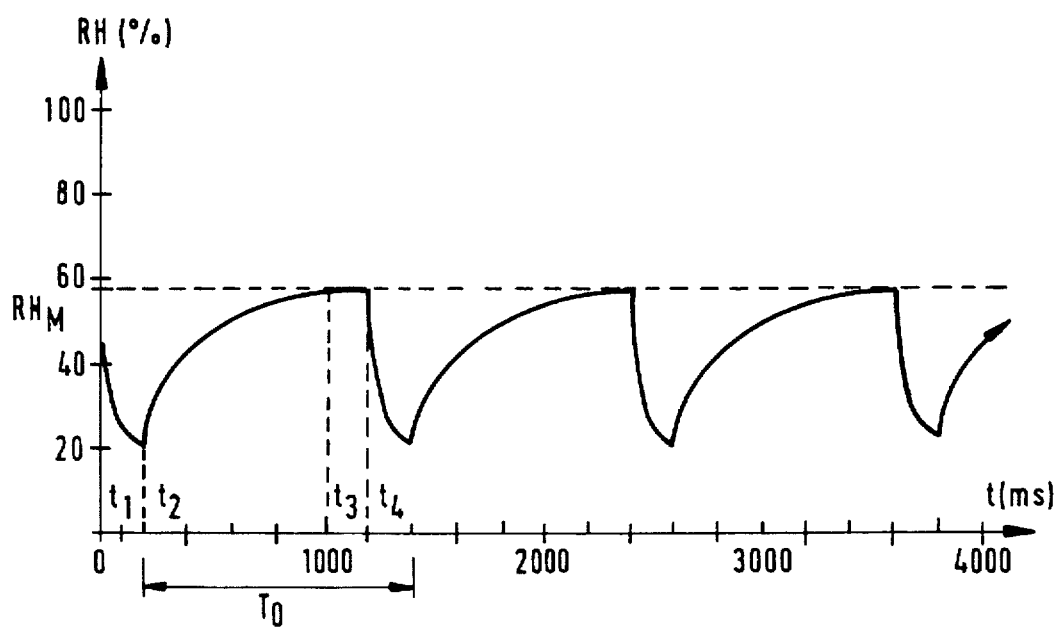
FIG. 11 shows the measurement signal of the humidity measurement of the system as shown in FIG. 10 as a function of time.
Figure 12:
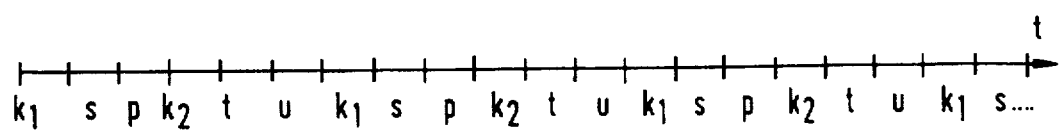
FIG. 12 illustrates the measurement sequences of the system as shown in FIG. 10 on the horizontal time axis of FIG. 11.
Figure 13:
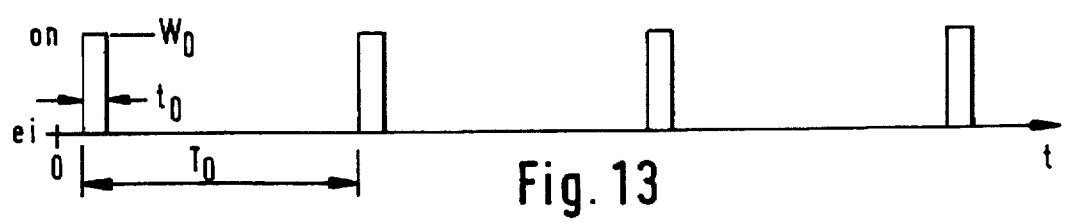
FIG. 13 shows the heating that is used in the measurement system as shown in FIGS. 10, 11 and 12 and that is pulsated in accordance with the invention on the horizontal time axis of FIGS. 11 and 12.

FIGS. 11, 12 and 13 are more detailed illustrations of the operation of the system as shown in FIG. 10. FIG. 11 is a graphic illustration of a typical measurement signal $RH_R$ received from the detector 10, which signal varies in sawtooth-wave form. At the time $t_1$, the heating power $W_0=I^2 \times R$ of the detector is switched on, and it remains on during the period of time $t_0$, i.e. until the point of time $t_2$, at which time the measurement signal $RH_R$ received from the detector is at the minimum. The heating power $W_0$ is typically in the range of $W_0 \approx 1 \ldots 100$ W, preferably in the range of $W_0 \approx 2 \ldots 10$ W. When the heating is switched off, the active film 12 in the detector 10 starts cooling, and then the reading of the detector 10 increases exponentially and approaches the correct value $RH_M$ of relative humidity. The "reading" of the detector is carried out during the time period $t_3 \ldots t_4$ (stage u in FIG. 12), by which time the detector 19 has had time to cool and to be stabilized, because of its little thermal mass, sufficiently close to the temperature of the environment, in which situation the detector 10 provides a correct reading= $RH_M$ of relative humidity without measurement and compensation of temperature. The measurement stage $t_3 \ldots t_4$ is followed by a new stage of heating of the detector 10, and the steps stated above are repeated in the cycles $T_0$ in the way shown in FIGS. 11, 12 and 13.

As is seen best from FIGS. 11 and 13, the duration $t_0$ of the heating stage is just a fraction of the duration $T_0$ of the measurement cycle $T_0$, because of which the stabilization and cooling of the measurement detector 10, as shown in FIG. 11, is achieved between the heating cycles. The duration of a measurement cycle is in radiosondes typically of an order of $T_0=0.2 \ldots 2$ seconds. When one detector is used, the duration of a heating cycle $t_0$ is typically of an order of $t_0 \approx 1$ ms $\ldots 100$ ms. The ratio $T_0/t_0$ is, as a rule, chosen in the range of $T_0/t_0 \approx 10 \ldots 3000$, preferably in the range of $T_0/t_0 \approx 100 \ldots 250$.

In the embodiment as shown in FIGS. 10, 11, 12 and 13, a detector 10 of a size as small as possible is used, whose size is preferably similar to that illustrated in FIGS. 1 or 2 and whose thermal mass is little, and which is additionally of low weight and of low cost of manufacture and, thus, particularly suitable for disposable sondes. In a system as shown in FIGS. 7 and 8, an equally rapid detector is not necessarily needed as in the construction as shown in FIGS. 10, 11, 12 and 13, in which case it is possible to use detector constructions similar, for example, to those shown in FIGS. 3, 4 and 5. On the other hand, the construction as shown in FIG. 6 is best suitable for systems in which the humidity is measured constantly, i.e. the detecting of the capacitance $C_M$ is constant and not cyclic, but, on the contrary, the heating of the component capacitances $C_1 \ldots C_N$ is cyclic and alternating.

The invention can be combined with a feature by whose means freezing or formation of frost or presence of condensed water on or in the vicinity of the active face of the detector can be detected. This feature can be accomplished, e.g., by means of a wiring similar to that shown in FIG. 14, whose operation is characterized by measurement of the rate of heating or equivalent of the heating resistor, for example of the heating resistor 15 present in the constructions as shown in FIGS. 4 and 5.

Figure 14:
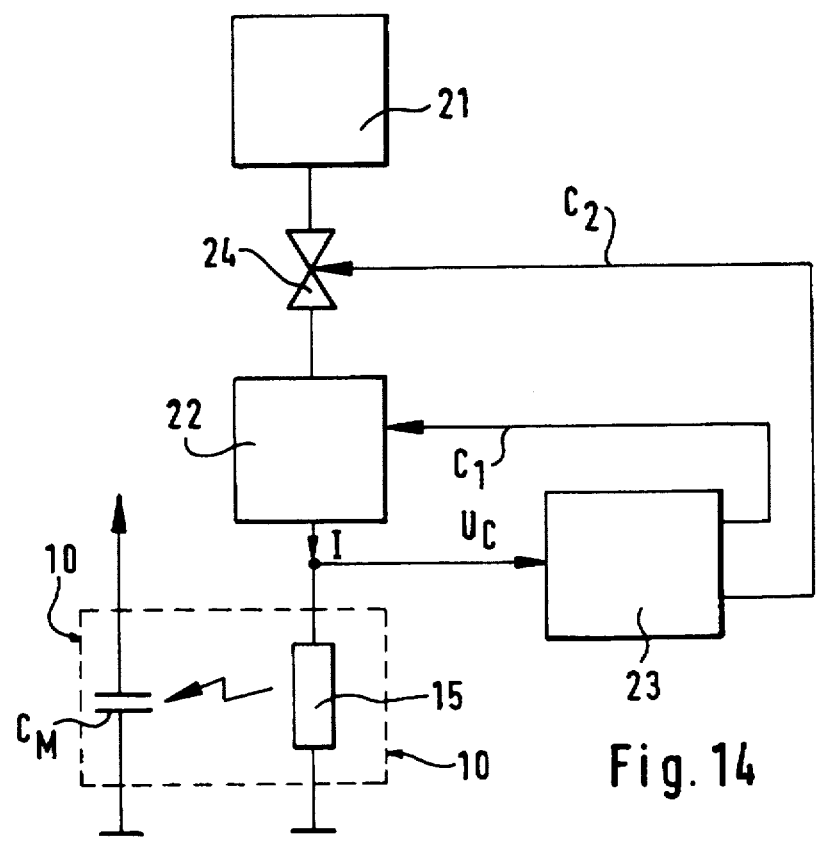
FIG. 14 shows an exemplifying embodiment of an electronics wiring by whose means it can be detected if there is ice or moisture on a detector as shown, for example, in FIGS. 4A, 4B or 5A, 5B.

The wiring shown in FIG. 14 comprises a feed unit 21 for heating power and a unit 23 for detecting the requirement of heating. By means of the unit 23, based on the rate of change in the resistance of the heating resistor 15, the requirement of heating is detected on the basis of the input signal $U_c$ of the unit 23. The unit 23 gives the heating-power regulation unit 22 and/or the unit 24 for regulation of the period of the heating pulse (optional) regulation signals $c_1$ and $c_2$. The operation of the unit 23 is based on the fact that, if there is condensed water, frost or ice in connection with the heating resistor 15 and in connection with the detector capacitance $C_M$ connected with said resistor 15, after the switching-on of the heating pulse, the rate of increase of the resistance of the heating resistor 15 is substantially slower than in a situation in which there is no condensed water, frost or ice on or near the heating resistor 15 and the active face of the detector capacitance $C_M$, because said water, frost and ice contribute to the formation of a thermal mass that retards the heating of the detector resistor 15. At the beginning of the heating stage, when it is noticed that the rate of increase of the detector resistance 15, which can be indicated, e.g. with an invariable current I, as a rate of increase in the voltage $U_c$, or in an equivalent way, is higher than a certain threshold value, the heating is discontinued under control by the signals $c_1$ and/or $c_2$ of the unit 23. On the other hand, if the rate of heating of the resistor 15 and the rate or increase in its resistance are lower than said threshold value, the periodic heating of the detector resistance 15 in accordance with the invention is continued under control by the regulation signals $c_1$ and/or $e_2$ of the unit 23 until said threshold value is surpassed and/or while following a preset sequence.

In the following, the patent claims will be given, and the various details of the invention may show variation within the scope of the inventive idea defined in said claims and differ from the details that have been described above for the sake of example only.

We claim:

1. Method for measurement of relative humidity by using a combination of detectors ($10_1$, $10_2$, 10P) in each of which detectors, between the capacitor plates, an insulating material (12) is used, whose permittivity is a function of the amount of water vapor absorbed by said insulating material (12), and in which method said combination of detectors is heated in order to remove any ice, frost, or condensed humidity deposited on the face or in the environment of the detector, each detector characterized by a number of component capacities ($C_1 C_2 \ldots C_N$) which are connected so as to form a detector capacitance ($C_M$) to be measured and comprising the steps of:

periodically heating the detector capacitance ($C_M$) or a part ($C_1 \ldots C_N$) of same, in time or in place, by means of electric current (I);

detecting the detector capacitance ($C_M$) without measurement of the detector temperature after the detector capacitance or a part ($C_1 \ldots C_N$) of same as cooled down substantially to the temperature of the environment;

employing at least two separate detectors ($10_1$, $10_2$) or a coupling of several component detectors ($C_1 \ldots C_N$) in parallel;

heating each detector in its turn, when several separate detectors ($10_1$, $10_2$) are used; and detecting the relative humidity substantially on the basis of a detector ($10_1$, $10_2$) or its component detectors ($C_1 \ldots C_N$) that has substantially cooled after said heating.

2. Method as claimed in claim 2, characterized in that, in the method, a number of component capacitances ($C_1 \ldots C_N$) connected in parallel are used, to each of which component capacitances the heating current (I) is connected in a rotating sequence alternatingly, and that the capacitance ($C_M$) to be measured is detected from the terminals ($c_1$, $c_2$) of the detector assembly connected in parallel, in which case, when N components of component detectors ($C_1 \ldots C_N$) are used, the proportion of a detector that is heated or that is to be heated in the total capacitance ($C_M$) of the detector is just one part per N (FIG. 6).

3. Method as claimed in claim 2, characterized in that the capacitance ($C_M$) is measured substantially constantly, and that the component capacitances ($C_1 \ldots C_N$) are heated in a certain repeatable cycle ($T_0$) alternatingly during a period of time $t_0$, which is $t_0 \approx T_0/N$.

4. Method for measurement of relative humidity by using a capacitive humidity (10) in which detector, between the capacitor plates, an insulating material (12) is used, whose permittivity is a function of the amount of water vapor absorbed by said insulating material (12), and in which method said detector (10) is heated in order to remove any ice, frost, or condensed humidity deposited on the face or in the environment of the detector, characterized by a number of component capacitances ($C_1 C_2 \ldots C_N$) which are connected so as to form a detector capacitance ($C_M$) to be measured and comprising the steps of periodically heating the detector capacitance ($C_M$) or a part ($C_1 \ldots C_N$) of same, in time or in place, by means of electric current (I), using a heating period ($t_0$) which is a fraction of a measurement cycle ($T_0$) off the detector;

detecting ($t_3 \ldots t_4$) the detector capacitance ($C_M$) after the heating period ($t_0$) in a final stage of the measurement cycle ($T_0$) without measuring the detector temperature after the detector capacitance or a part ($C_1 \ldots C_N$) of same has had time to be stabilized after said heating period ($t_0$) and to cool down substantially to the temperature of the environment off the detector (10), at which time the detector shows a correct humidity reading ($RH_M$); and before beginning the heating of the detector, sensing the presence of any ice, frost, or condensed humidity deposited in connection with the detector (10) by observation of deviant spurious, erratic capacitance measurements over a short period of time compared to said measurement period, or of non-varying capacitance measurements over a longer period of time on the order of or exceeding said measurement period.

5. Method as claimed in claim 4, characterized in that said detecting of freezing, frost formation and/or wetting on the detector (10) is carded out on the basis of measurement of a change in the rate of heating and/or in the specific resistance of a resistor piece (15) placed in connection with the detector (FIG. 14).

6. A capacitive humidity detector intended for carrying out a method for measurement of relative humidity by using a capacitive humidity detector (10) or a combination of detectors ($10_1$, $10_2$; 10P), in which detector, between the capacitor plates, an insulating material (12) is used, whose permittivity is a function of the amount of water vapor absorbed by said insulating material (12), and in which method said detector (10) or combination of detectors is heated in order to remove any ice, frost, or condensed humidity deposited on the face or in the environment of the detector, the detector capacitance ($C_M$) or a part ($C_1 \ldots C_N$) of same is periodically heated, in time or in place, by means of electric current (I); and that the detecting of the detector capacitance ($C_M$) is carried out without measurement of the detector temperature after the detector capacitance or a part ($C_1 \ldots C_N$) of same has cooled down substantially to the temperature of the environment where a number of component capacitances ($C_1, C_2 \ldots C_N$) are connected so as to form the detector capacitance ($C_M$) to be measured, with, the detector comprising:

a substrate (11) made of an insulating material, onto which substrate the contact patterns necessary for the formation and connecting of the detector capacitance have been applied;

an active insulation film (12) between the detector capacitance electrodes, the permittivity of the insulation film being a function of the amount of water absorbed by said film (12);

a surface contact (14) applied onto the film (12), the surface contact being an electrically conductive surface electrode (14) penetrable by water, a contact pattern (13b) connected to said surface electrode;

said surface electrode (14) is connected with the contact patterns (13b, 15a) so that an electric current (I) that heats the detector (10) also passes through said patterns into said surface electrode (14); and the surface-electrode heating resistor (R) and the capacitance ($C_M$) to be measured have one common terminal ($c_2$, $r_2$).

7. A humidity detector intended for carrying out a method for measurement of relative humidity by using a capacitive humidity detector (10) or a combination of detectors ($10_1$, $10_2$; 10P), in which detector, between the capacitor plates, an insulating material (12) is used, whose permittivity is a function of the; amount of water vapor absorbed by said insulating material (12), and in which method said detector (10) or combination of detectors is heated in order to remove any ice, frost, or condensed humidity deposited on the face or in the environment of the detector, the detector capacitance ($C_M$) or a part ($C_1 \ldots C_N$) of same is periodically heated, in time or in place, by means of electric current (I); and that the detecting of the detector capacitance ($C_M$) is carried out without measurement of the detector temperature after the detector capacitance or a part ($C_1 \ldots C_N$) of same has cooled down substantially to the temperature of the environment, the detector comprising:

a number of component capacitances ($C_1, C_2 \ldots C_N$), which are connected so as to form a detector capacitance ($C_M$) to be measured; and each component capacitance ($C_1, C_2 \ldots C_N$) is provided with a heating resistor ($R_1 \ldots R_N$) of its own, into which resistors heating currents ($I_1 \ldots I_N$) can be passed separately so as to separately heat each of the component capacitances ($C_1 \ldots C_N$).

8. Detector as claimed in claim 7, characterized in that the detector comprises a number N of capacitances connected in parallel, and that $N \approx 2 \ldots 20$, preferably $N = 5 \ldots 10$.

* * * * *